United States Patent [19]

Bristow et al.

[11] Patent Number: 4,933,173

[45] Date of Patent: Jun. 12, 1990

[54] ORAL PREPARATIONS

[75] Inventors: Neil J. Bristow, New South Wales, Australia; Peter Carter, Burton; Bryony E. Coulson, Port Sunlight, both of Great Britain; Michael A. Trevethan, Bebington, Great Britain

[73] Assignee: Unilever Patent Holdings B.V., Rotterdam, Netherlands

[21] Appl. No.: 354,657

[22] Filed: May 19, 1989

[30] Foreign Application Priority Data

May 19, 1988 [GB] United Kingdom ............... 8811829

[51] Int. Cl.$^5$ ........................... A61K 7/16; A61K 7/22
[52] U.S. Cl. ........................................ 424/54; 424/49; 424/57
[58] Field of Search ............................. 424/49, 54–57

[56] References Cited

U.S. PATENT DOCUMENTS

| 3,122,483 | 2/1964 | Rosenthal | 167/93 |
| 3,699,220 | 10/1972 | Westrate et al. | 424/57 |
| 3,699,221 | 10/1972 | Schole et al. | 424/54 |
| 3,863,006 | 1/1975 | Hodosh | 424/49 |
| 4,327,079 | 4/1982 | Aoki | 424/57 |
| 4,634,589 | 1/1987 | Scheller | 424/49 |

FOREIGN PATENT DOCUMENTS

| 575035 | 7/1988 | Australia . |
| 999238 | 11/1976 | Canada . |
| 1212627 | 10/1986 | Canada . |
| 95871 | 12/1983 | European Pat. Off. . |
| 254452 | 1/1988 | European Pat. Off. . |
| WO/823008 | 9/1982 | PCT Int'l Appl. . |
| 8500123 | 9/1985 | PCT Int'l Appl. . |
| WO/877615 | 12/1987 | PCT Int'l Appl. . |
| 1586915 | 3/1981 | United Kingdom . |
| 2188548 | 10/1987 | United Kingdom . |

*Primary Examiner*—Shep K. Rose
*Attorney, Agent, or Firm*—Milton L. Honig

[57] ABSTRACT

The present invention relates to oral preparations having anti-caries activity. The compositions comprise a water-soluble casein material or sodium trimetaphosphate as an anti-caries agent, and a particulate hydroxyapatite as a compatible abrasive material.

5 Claims, No Drawings

ORAL PREPARATIONS

This invention relates to oral preparations and in particular to oral preparations having an anti-caries activity.

It is well known that various water-soluble fluorine-containing compounds are useful for combating dental caries. Examples are sodium monofluorophosphate, sodium fluoride and stannous fluoride.

There have been proposals to combat dental caries through the use in oral compositions of agents which do not contain fluorine.

It is known from EP-A-73 210 (University of Melbourne and the Victorian Dairy Industry Authority) to employ certain water-soluble casein materials as anti-caries agents. In particular it is suggested to use alpha$_s$-casein, beta-casein, water-soluble salts thereof and water-soluble salts of whole casein. These casein materials are phosphoproteins and contain the aminoacid sequence (X—Y—Z), where X and Z are a phosphoserine, phosphothreonine, phosphotyrosine, glutamate or aspartate and Y is any aminoacid. Dentifrices containing casein materials are disclosed in an amount of from 0.5% to 10% by weight. The water-soluble material may also contain a plurality of units each having the aminoacid sequence (X—Y—Z), where X, Y and Z are as stated above.

EP-A-166 055 (University of Melbourne and the Victorian Dairy Industry Authority) contains a similar disclosure save that in this case the casein material employed is a casein digest. In particular, a casein digested by means of an enzyme, for example, trypsin, pepsin, chymotrypsin or pronase, to produce shorter chain phosphopeptides is disclosed.

It has been proposed in WO 87/07615 (University of Melbourne and the Victorian Dairy Industry Authority) that phosphopeptides or salts thereof having from 5 to 30 aminoacids including the sequence A—B—C—D—E, where A, B, C, D and E are independently phosphoserine, phosphothreonine, phosphotyrosine, phosphohistidine, glutamate and aspartate, may be used to inhibit caries and gingivitis. Sources of such phosphopeptides include casein, particular $\alpha_s$-casein or $\beta$-casein or salts thereof such as sodium caseinates, phosvitin and phosphoproteins from cereals, nuts, vegetables, soyabean and meat, which have been enzymically digested with trypsin, pepsin, chymotrypsin, papain, thermolysin or pronase. Also calcium phosphate complexes of the tryptic digest of casein are disclosed as anti-caries agents. Compositions containing the phosphopeptide or salt thereof at 0.01% to 10% by weight are disclosed.

In U.S. Pat. No. 4 132 773 (Best et al.) is disclosed an anti-caries toothpaste comprising a silica xerogel abrasive and sodium trimetaphosphate.

In the formulation of products containing agents to enhance or maintain oral health it is important that the potential efficacy of such agents is not jeopardised by interaction with other components of the oral product. It is well known to those skilled in the art that the solid particulate abrasive agent may have a propensity for binding active agents thus reducing the effectiveness of the product.

It is an object of the invention to formulate an improved anti-caries composition which does not include a fluorine-containing ingredient.

Accordingly, there is provided by the present invention a substantially fluorine free anti-caries oral composition comprising finely-divided hydroxyapatite and an anti-caries agent selected from water-soluble casein materials and sodium trimetaphosphate.

We have now found that finely divided hydroxyapatite is an abrasive agent that has a high degree of compatibility with casein materials and with sodium trimetaphosphate. The suitablility of finely divided hydroxyapatite as a dentifrice abrasive is already known from CA-A-999 238, US-A-4 634 589 and US-A-4 327 079 but its use in products containing a casein material or sodium trimetaphosphate as active agent has not previously been suggested.

The hydroxyapatite abrasive is used in a particle size giving satisfactory cleaning without being harmful to the tooth surface when used in appropriate amounts in oral compositions of the invention. The average particle size will usually be in the range from about 1 micron to about 15 microns, preferably 2 to 10 and particularly preferably about 3 to about 10 microns.

Preferred particulate hydroxyapatites for use in oral compositions of this invention are synthetic hydroxyapatites of high purity consisting of at least 92% of $Ca_{10}(PO_4)_6(OH)_2$. The remainder will comprise mainly bound water (typically 6% maximum) and a minor amount of calcium carbonate (typically 2% minimum). A process for the preparation of hydroxyapatites is described in GB-A-1 586 915 (British Charcoals & Macdonalds).

A highly pure synthetic hydroxyapatite available15 commercially is that sold under the trade name CAPTAL by British Charcoals & Macdonalds of Greenock, Scotland.

This hydroxyapatite contains about 97% $Ca_{10}(PO_4)_6(OH)_2$. The remaining 3% is mostly bound water with approximately 0.3% calcium carbonate.

The amount of the hydroxyapatite present in oral compositions of this invention will range from 1–50%, usually from about 2% to about 20%, preferably from 3% to 15%, by weight of the oral composition.

The amount of the water-soluble casein derivative may range from about 0.01& to about 10% by weight, and the amount of sodium trimetaphosphate may range from about 0.5% to about 5% by weight.

Additional benefits which are already associated with the use of hydroxyapatite in the prior literature are a desensitising activity for users having hypersensitive teeth.

Together with the hydroxyapatite and casein material and/or sodium trimetaphosphate, the oral product of the invention will contain other conventional ingredients well known to those skilled in art depending on the form of the oral product. For instance, in the case of an oral product in the form of a dentifrice cream or paste, the product will comprise an humectant-containing liquid phase and a binder or thickener which acts to maintain the particulate solid abrasive in stable suspension in the liquid phase. A surfactant and a flavouring agent are also usual ingredients of commercially acceptable dentifrices.

Humectants commonly used are glycerol and sorbitol syrup (usually comprising an approximately 70% solution). However, other humectants are known to those in the art including propylene glycol, lactitol and hydrogenated corn syrup. The amount of humectant will generally range from about 10 to 85% by weight of the dentifrice. The remainder of the liquid phase will consist substantially of water.

Likewise, numerous binding or thickening agents have been indicated for use in dentifrices, preferred ones being sodium carboxymethylcellulose and xanthan gum. Others include natural gum binders such as gum tragacanth, gum karaya and gum arabic, Irish moss, alginates and carrageenans. Silica thickening agents include the silica aerogels and various precipitated silicas. Mixtures of binding and thickening agents may be used. The amount of binder and thickening agent included in a dentifrice is generally between 0.1 and 10% by weight.

It is usual to include a surfactant in a dentifrice and again the literature discloses a wide variety of suitable materials. Surfactants which have found wide use in practice are sodium lauryl sulphate, sodium dodecylbenzene sulphonate and sodium lauroylsarcosinate. Other anionic surfactants may be used as well as other types such as cationic, amphoteric and nonionic surfactants. Surfactants are usually present in an amount of from 0.5 to 5% by weight of the dentifrice.

Flavours that are usually used in dentifrices are those based on oils of spearmint and peppermint. Examples of other flavouring materials used are menthol, clove, wintergreen, eucalyptus and aniseed. An amount of from 0.1% to 5% by weight is a suitable amount of flavour to incorporate in a dentifrice.

The oral compositions of the invention may also comprise a proportion of a supplementary abrasive agent such as silica, alumina, hydrated alumina, calcium carbonate, anhydrous dicalcium phosphate, dicalcium phosphate dihydrate and water-insoluble sodium metaphosphate.

The oral composition of the invention may include a wide variety of optional ingredients. These include an anti-plaque agent such as an antimicrobial compound for example chlorhexidine or 2,4,4'-trichloro-2'-hydroxy-diphenyl ether, or a zinc compound (see EP-A-161 898); an anti-tartar ingredient such as a condensed phosphate, e.g. an alkali metal pyrophosphate, hexametaphosphate or polyphosphate, (see US-A-4 515 772 and US-A-4 627 977) or zinc citrate (see US-A-4 100 269); sweetening agent, such as saccharin; an opacifying agent, such as titanium dioxide; a preservative, such as formalin; a colouring agent; or pH-controlling agent such as an acid, base or buffer, such as benzoic acid.

For a fuller discussion of the formulation of oral compositions, reference is made to Harry's Cosmeticology, Seventh Edition, 1982, Edited by J.B. Wilkinson and R.J. Moore, pages 609 to 617.

The invention also relates to a method of combating dental caries which consists in applying to the teeth, such as by brushing, an oral composition according to the invention.

The following Examples illustrate the invention. Percentages and parts are by weight.

EXAMPLES 1-2

Toothpastes are prepared from the following ingredients:

| Ingredient | Example: | 1 | 2 |
|---|---|---|---|
| Hydroxyapatite | | 5.00 | 5.00 |
| Silica aerogel (Gasil 23) | | 10.00 | 10.00 |
| Sorbitol syrup | | 40.00 | 40.00 |
| Sodium lauryl sulphate | | 1.50 | 1.50 |
| Sodium carboxymethylcellulose | | 1.00 | 1.00 |
| Sodium caseinate | | 5.00 | — |
| Calcium salt of Ti phosphopeptide according to WO 87/07615 | | — | 1.00 |
| Sodium saccharin | | 0.20 | 0.20 |
| Titanium dioxide | | 1.00 | 1.00 |
| Formalin | | 0.04 | 0.04 |
| Flavour | | 1.00 | 1.00 |
| Water | | to 100.00 | to 100.00 |

EXAMPLE 3

A toothpaste is prepared from the following ingredients:

| Ingredient | % |
|---|---|
| Hydroxyapatite | 5.00 |
| Silica aerogel (Gasil 23) | 10.00 |
| Sorbitol syrup | 40.00 |
| Sodium lauryl sulphate | 1.50 |
| Sodium carboxymethylcellulose | 1.00 |
| Sodium trimetaphosphate | 3.00 |
| Sodium saccharin | 0.20 |
| Titanium dioxide | 1.00 |
| Formalin | 0.04 |
| Flavour | 1.00 |
| Water | to 100.00 |

EXAMPLES 4 and 5

Toothpastes are made from the ingredients indicated below.

| Ingredient | Example: | 4 | 5 |
|---|---|---|---|
| Hydroxyapatite | | 10.0 | 10.0 |
| Thickening silica | | 10.0 | 10.0 |
| Sorbitol syrup (70% solution) | | 40.0 | 40.0 |
| Sodium lauryl sulphate | | 1.5 | 1.5 |
| Sodium carboxymethylcellulose | | 1.0 | 1.0 |
| Sodium caseinate | | 5.0 | — |
| Sodium trimetaphosphate | | — | 3.0 |
| Triclosan | | 0.2 | — |
| Zinc citrate trihydrate | | 0.5 | — |
| Glucoseoxidase | | — | 0.3 |
| Amyloglucosidase | | — | 1.2 |
| Potassium thiocyanate | | — | 0.02 |
| Sodium saccharin | | 0.2 | 0.2 |
| Titanium dioxide | | 1.0 | 1.0 |
| Formalin | | 0.04 | 0.04 |
| Flavour | | 1.0 | 1.0 |
| Water | | to 100.0 | to 100.0 |

What is claimed is:

1. A substantially fluorine-free oral preparation having an anti-caries activity, comprising a watersoluble casein material or sodium trimetaphosphate as anti-caries agent, and a particulate abrasive material, wherein the particulate abrasive material is or comprises hydroxyapatite.

2. A preparation according to claim 1, wherein the hydroxyapatite has an average particle size of from 1 to 15 microns.

3. A preparation according to claim 1, wherein the hydroxyapatite is a synthetic hydroxyapatite which consists for at least 92% by weight of $Ca_{10}(PO_4)_6(OH)_2$.

4. A preparation according to claim 1, wherein the hydroxyapatite is present in an amount of 1–50% by weight.

5. A preparation according to claim 1, containing from 0.01 to 10% by weight of the water-soluble casein material or 0.5 to 5% by weight of the sodium trimetaphosphate.

* * * * *